(12) United States Patent
Rosenberg

(10) Patent No.: US 10,300,068 B2
(45) Date of Patent: May 28, 2019

(54) METHOD OF TREATING INSOMNIA

(71) Applicant: Leon I. Rosenberg, Cherry Hill, NJ (US)

(72) Inventor: Leon I. Rosenberg, Cherry Hill, NJ (US)

(*) Notice: Subject to any disclaimer, the term of this patent is extended or adjusted under 35 U.S.C. 154(b) by 0 days.

(21) Appl. No.: 15/939,953

(22) Filed: Mar. 29, 2018

(65) Prior Publication Data

US 2018/0221373 A1 Aug. 9, 2018

Related U.S. Application Data

(62) Division of application No. 15/268,311, filed on Sep. 16, 2016, now Pat. No. 9,962,387.

(60) Provisional application No. 62/219,337, filed on Sep. 16, 2015.

(51) Int. Cl.
| | | |
|---|---|---|
| *A61K 31/519* | (2006.01) | |
| *A61K 31/4985* | (2006.01) | |
| *A61K 31/506* | (2006.01) | |
| *A61K 31/53* | (2006.01) | |
| *A61K 31/7048* | (2006.01) | |

(52) U.S. Cl.
CPC ........ *A61K 31/519* (2013.01); *A61K 31/4985* (2013.01); *A61K 31/506* (2013.01); *A61K 31/53* (2013.01); *A61K 31/7048* (2013.01)

(58) Field of Classification Search
CPC ................ A61K 31/519; A61K 31/506; A61K 31/4985; A61K 31/53; A61K 31/7048
USPC ....................................................... 514/262.1
See application file for complete search history.

(56) References Cited

PUBLICATIONS

Cialis Package Label. Eli Lilly and Company 2003, 2011.
Viagra Package Label. Pfizer Labs 2014.
Masters, William and Johnson, Virginia E. Human Sexual Response. Ishi Press International, 1966.
Levitra Package Label. Bayer HealthCare Pharmaceuticals Inc. Copyright 2014.
Belsomra Package Label. Merck Sharp & Dohme Corp., a subsidiary of Merck & Co., Inc. Copyright 2014.
Stendra. FDA Package Insert, p. 2. VIVUS, Inc. 2017. https://medialibrary.org/lib/rx/meds/stendra-2/page/2/.
Zhang, Ruilan et al. Sildenafil (Viagra) Induces Neurogenesis and Promotes Functional Recovery After Stroke in Rats. American Heart Association, Inc. 2002. http://stroke.ahajournals.org/content/33/11/2675.
Zhang, Ruilan et al. Nitric Oxide Enhances Angiogenesis via the Synthesis of Vascular Endothelial Growth Factor and cGMP After Stroke in the Rat. American Heart Association, Inc. 2003. http://circres.ahajournals.org/content/92/3/308.
Ambian Package Label, Sanofi-Aventis U.S. LLC, Oct. 2014.
Watkins, Crystal C. et al. Insulin Restores Neuronal Nitric Oxide Synthase Expression and Function that is lost in Diabetic Gastropathy. The Journal of Clinical Investigation, vol. 106, No. 3, Aug. 2000.
Michelakis, Evangelos D. et al. Long Term Treatment With Oral Sildenafil is Safe and Improves Functional Capacity and Hemodynamics in Patients With Pulmonary Arterial Hypertension. American Heart Association, Inc. Copyright 2003. http://circ.ahajournals.org/content/108/17/2066.
Ghofrani, Hossein et al. Sildenafil for treatment of lung fibrosis and pulmonary hypertension: a randomised controlled trial. The Lancet, vol. 360, No. 9337, p. 895-900, Sep. 21, 2002. http://www.thelancet.com/journals/lancet/articles/PIIS0140-6736.
Ghofrani, Hossein et al. Sildenafil for Long-Term Treatment of Nonoperable Chronic Thromboembolic Pulmonary Hypertension. American Journal of Respiratory and Critical Care Medicine, vol. 167, 2003.
Ghofrani, Hossein et al. Oral Sildenafil as Long-Term Adjunct Therapy to Inhaled Iloprost in Severe Pulmonary Arterial Hypertension. Journal of the American College of Cardiology. vol. 42, No. 1. Elsevier Inc. 2003.
Halcox, Julian et al. The Effect of Sildenafil on Human Vascular Function, Platelet Activation, and Myocardial Ischemia. Journal of the American College of Cardiology. vol. 40, No. 7. Elsevier Science Inc. 2002.
Bianco, Alessandro et al. Effect of Sildenafil on Diabetic Gastropathy. Diabetes Care, vol. 25, No. 10. pp. 1888-1889. Oct. 2002.

*Primary Examiner* — Jeffrey H Murray
(74) *Attorney, Agent, or Firm* — Kim IP Law Group PLLC

(57) ABSTRACT

Methods for treating insomnia are disclosed. The methods are directed to administering a pharmaceutically effective amount of phosphodiesterase 5 (PDE5) inhibitor to a male individual suffering from insomnia. In addition, due to the PDE5 inhibitor positive effects on addressing erectile dysfunction (ED) in males, the present methods are directed to treating insomnia in patients that also suffer from ED by administering a pharmaceutically effective amount of a PDE5 inhibitor.

18 Claims, No Drawings

METHOD OF TREATING INSOMNIA

CROSS REFERENCE TO RELATED APPLICATIONS

This application is a divisional of U.S. patent application Ser. No. 15/268,311 filed Sep. 16, 2016, entitled "METHOD OF TREATING INSOMNIA," which claims the benefit of U.S. Provisional Application No. 62/219,337 filed Sep. 16, 2015, entitled "METHOD OF TREATING INSOMNIA," the entire disclosures of which are hereby incorporated by reference for all purposes.

BACKGROUND OF THE INVENTION

Insomnia and other sleep problems are among the most common complaints dealt with by physicians, such as primary care physicians and psychiatrists. It is estimated that about 33% of the general population and up to 50% of older adults suffer from insomnia and other sleep-related disorders. Insomnia is generally defined and categorized into four categories: 1) trouble falling asleep (sleep onset—difficulty falling asleep—DFA); 2) trouble staying asleep (sleep maintenance—middle insomnia—MI); 3) waking up too early (early morning awakening—EMA); and 4) poor quality sleep (nonrestorative sleep).

There are various recognized problems with the state of the art in methods for treating insomnia. With the current state of the art, a current state of the art medication needs to be taken each time there is insomnia and each time the current state of the art medication is taken there are risks of side effects. The present state of the art for the treatment of insomnia includes medication and non-medication approaches. The present state of the art for the treatment of insomnia includes the following categories of medications and other treatments as 1.5 million Americans use complementary and alternative therapies to treat insomnia: 1) Benzodiazepine (short acting medications): Ativan (lorazepam), Xanax (alprazolam), Librium (chlordiazepoxide), Halcion (triazolam), Restoril (temazepam), Serax (oxazepam), Prosom (estazolam); 2) Benzodiazepine and Sedative hypnotics (long acting medications): Valium (diazepam), Dalmane (flurazepam), Klonopin (clonazepam), chloral hydrate, Doral (quazepam); 3) Non-benzodiazepine hypnotics: Sonata (zaleplon), Ambien (zolpidem), Rozerem (ramelteon), Lunesta (eszopiclone); 4) Antihistamine: Atarax (hydroxyzine HCL), Vistaril (hydroxyzine pamoate), Benadryl (diphenhydramine), Unisom (doxylamine); 5) Melatonin activating agents: Rozerem (ramelteon); 6) Barbiturates: Phenobarbital, Seconal (secobarbital), Tuinal; 7) Natural substances and over the counter (OTC) preparations: Tryptophan, Melatonin, valerian root, kava, tryptophan and 5-L-5-hydroxytryptophan, chamomile tea, lip balm; 8) Antidepressants: Doxepin, trazodone, amitriptyline, mirtazapine; 9) Antipsychotics: Seroquel, Zyprexa; and 10) Orexin Inhibitors: Belsomra (suvorexant).

Some of the problems with the state-of-the-art include the following non-comprehensive list of side effects from the existing medication: 1) Benzodiazepine: confusion, addiction, paradoxical reaction, drug/drug interactions, abuse, over sedation, drug/food interactions, diversion; 2) Benzodiazepine and Sedative hypnotics: confusion, addiction, diversion, paradoxical reaction, drug/drug interactions, abuse, over sedation, drug/food interactions; 3) Non-benzodiazepine hypnotics: confusion, addiction, diversion, paradoxical reaction, drug/drug interactions, abuse, over sedation, drug/food interactions; 4) Antihistamine: confusion, paradoxical reaction, drug/drug interactions, abuse, over sedation, drug/food interactions; 5) Melatonin activating agents: lack of response, confusion, paradoxical reaction, drug/drug interactions, abuse, over sedation, drug/food interactions, dry mouth; 6) Barbiturates: confusion, addiction, paradoxical reaction, drug/drug interactions, abuse, over sedation, drug/food interactions; 7) Tryptophan: confusion, addiction, paradoxical reaction, drug/drug interactions, abuse, over sedation, drug/food interactions; 8) Antidepressants including doxepin, trazodone, amitriptyline, mirtazapine: confusion, paradoxical reaction, manic reactions, priapism, anticholinergic delirium, drug/drug interactions, abuse, over sedation, drug/food interactions; 9) Antipsychotics including Seroquel: confusion, paradoxical reaction, drug/drug interactions, abuse, over sedation, drug/food interactions, weight gain, Diabetes Mellitus, Hyperlipidemia.

For adults over 60 years of age, studies show that the risks of prescribed sedative hypnotics far outweigh the benefits. A general recommendation is to only use sedative hypnotics 2 to 4 days per week. Dependence (a phenomenon akin to addiction), tolerance (needing more and more of a substance), and rebound insomnia (difficulty sleeping after medication is discontinued) are problems with sedative hypnotics. As a result, Consumer Reports noted for example that "chronic insomnia is undertreated and less than half of the people who need help actually get it." Perhaps this is because there are class effect warnings associated with the available medication treatments. These class effect warnings are a problem to both doctors prescribing the medication and patients taking the medication. Some of these warning include: 1) the medications are abusable medication; 2) the medications are addicting medication; 3) the medications are controlled drugs; 4) the medications are dangerous to mix with alcohol and other agents that affect the central nervous system; 5) the medications can cause sleep walking, sleep driving, sleep telephone calling; 6) the medications can cause memory loss; 7) the medications can cause central nervous system (CNS) issues; and 8) the medications have a driving warning.

As an example of the concern the authorities have about these types of medication, the following are excerpted from the FDA authorized package insert for Belsomra (suvorexant), a medication the FDA recently approved in 2014 for the treatment of insomnia:

2 DOSAGE AND ADMINISTRATION 2.1 Dosing Information

Use the lowest dose effective for the patient. The recommended dose for BELSOMRA is 10 mg, taken no more than once per night and within 30 minutes of going to bed, with at least 7 hours remaining before the planned time of awakening. If the 10 mg dose is well-tolerated but not effective, the dose can be increased. The maximum recommended dose of BELSOMRA is 20 mg once daily.

2.2 Special Populations

Exposure to BELSOMRA is increased in obese compared to non-obese patients, and in women compared to men. Particularly in obese women, the increased risk of exposure-related adverse effects should be considered before increasing the dose [see Clinical Pharmacology (12.3)].

2.3 Use with CNS Depressants

When BELSOMRA is combined with other CNS depressant drugs, dosage adjustment of BELSOMRA and/or the other drug(s) may be necessary because of potentially additive effects [see Warnings and Precautions (5.1)].

2.4 Use with CYP3A Inhibitors

The recommended dose of BELSOMRA is 5 mg when used with moderate CYP3A inhibitors and the dose generally should not exceed 10 mg in these patients. BELSOMRA is not recommended for use with strong CYP3A inhibitors [see Drug Interactions (7.2)].

2.5 Food Effect

Time to effect of BELSOMRA may be delayed if taken with or soon after a meal.

5.1 CNS Depressant Effects and Daytime Impairment

BELSOMRA is a central nervous system (CNS) depressant that can impair daytime wakefulness even when used as prescribed. Prescribers should monitor for somnolence and CNS depressant effects, but impairment can occur in the absence of symptoms, and may not be reliably detected by ordinary clinical exam (i.e., less than formal testing of daytime wakefulness and/or psychomotor performance). CNS depressant effects may persist in some patients for up to several days after discontinuing BELSOMRA.

BELSOMRA can impair driving skills and may increase the risk of falling asleep while driving. Discontinue or decrease the dose in patients who drive if daytime somnolence develops. In a study of healthy adults, driving ability was impaired in some individuals taking 20 mg BELSOMRA [see Clinical Studies (14.2)].

Although pharmacodynamic tolerance or adaptation to some adverse depressant effects of BELSOMRA may develop with daily use, patients using the 20 mg dose of BELSOMRA should be cautioned against next-day driving and other activities requiring full mental alertness. Patients taking lower doses of BELSOMRA should also be cautioned about the potential for driving impairment because there is individual variation in sensitivity to BELSOMRA.

Co-administration with other CNS depressants (e.g., benzodiazepines, opioids, tricyclic antidepressants, alcohol) increases the risk of CNS depression. Patients should be advised not to consume alcohol in combination with BELSOMRA because of additive effects [see Drug Interactions (7.1)]. Dosage adjustments of BELSOMRA and of concomitant CNS depressants may be necessary when administered together because of potentially additive effects. The use of BELSOMRA with other drugs to treat insomnia is not recommended [see Dosage and Administration (2.3)].

The risk of next-day impairment, including impaired driving, is increased if BELSOMRA is taken with less than a full night of sleep remaining, if a higher than the recommended dose is taken, if co-administered with other CNS depressants, or if co-administered with other drugs that increase blood levels of BELSOMRA. Patients should be cautioned against driving and other activities requiring complete mental alertness if BELSOMRA is taken in these circumstances.

5.2 Need to Evaluate for Co-morbid Diagnoses

Because sleep disturbances may be the presenting manifestation of a physical and/or psychiatric disorder, treatment of insomnia should be initiated only after careful evaluation of the patient. The failure of insomnia to remit after 7 to 10 days of treatment may indicate the presence of a primary psychiatric and/or medical illness that should be evaluated. Worsening of insomnia or the emergence of new cognitive or behavioral abnormalities may be the result of an unrecognized underlying psychiatric or physical disorder, and can emerge during the course of treatment with hypnotic drugs such as BELSOMRA.

5.3 Abnormal Thinking and Behavioral Changes

A variety of cognitive and behavioral changes (e.g., amnesia, anxiety, hallucinations and other neuro-psychiatric symptoms) have been reported to occur in association with the use of hypnotics such as BELSOMRA. Complex behaviors such as "sleep-driving" (i.e., driving while not fully awake after taking a hypnotic) and other complex behaviors (e.g., preparing and eating food, making phone calls, or having sex), with amnesia for the event, have been reported in association with the use of hypnotics. These events can occur in hypnotic-naïve as well as in hypnotic-experienced persons. The use of alcohol and other CNS depressants may increase the risk of such behaviors. Discontinuation of BELSOMRA should be strongly considered for patients who report any complex sleep behavior.

5.4 Worsening of Depression/Suicidal Ideation

In clinical studies, a dose-dependent increase in suicidal ideation was observed in patients taking BELSOMRA as assessed by questionnaire. Immediately evaluate patients with suicidal ideation or any new behavioral sign or symptom.

In primarily depressed patients treated with sedative-hypnotics, worsening of depression, and suicidal thoughts and actions (including completed suicides) have been reported. Suicidal tendencies may be present in such patients and protective measures may be required. Intentional overdose is more common in this group of patients; therefore, the lowest number of tablets that is feasible should be prescribed for the patient at any one time. The emergence of any new behavioral sign or symptom of concern requires careful and immediate evaluation.

5.5 Patients with Compromised Respiratory Function

Effect of BELSOMRA on respiratory function should be considered if prescribed to patients with compromised respiratory function. BELSOMRA has not been studied in patients with severe obstructive sleep apnea (OSA) or severe chronic obstructive pulmonary disease (COPD) [see Use in Specific Populations (8.6)].

5.6 Sleep Paralysis, Hypnagogic/Hypnopompic Hallucinations, Cataplexy-like Symptoms Sleep paralysis, an inability to move or speak for up to several minutes during sleep-wake transitions, and hypnagogic/hypnopompic hallucinations, including vivid and disturbing perceptions by the patient, can occur with the use of BELSOMRA.

Prescribers should explain the nature of these events to patients when prescribing BELSOMRA. Symptoms similar to mild cataplexy can occur, with risk increasing with the dose of BELSOMRA. Such symptoms can include periods of leg weakness lasting from seconds to a few minutes, can occur both at night and during the day, and may not be associated with an identified triggering event (e.g., laughter or surprise).

7 DRUG INTERACTIONS 7.1 CNS-Active Agents

When BELSOMRA was co-administered with alcohol, additive psychomotor impairment was demonstrated. There was no alteration in the pharmacokinetics of BELSOMRA [see Warnings and Precautions (5.1, 5.3) and Clinical Pharmacology (12.3)].

7.2 Effects of Other Drugs on BELSOMRA

Metabolism by CYP3A is the major elimination pathway for suvorexant. CYP3A Inhibitors Concomitant use of BELSOMRA with strong inhibitors of CYP3A (e.g., ketoconazole, itraconazole, posaconazole, clarithromycin, nefazodone, ritonavir, saquinavir, nelfinavir, indinavir, boceprevir, telaprevir, telithromycin and conivaptan) is not recommended [see Clinical Pharmacology (12.3)].

The recommended dose of BELSOMRA is 5 mg in subjects receiving moderate CYP3A inhibitors (e.g., amprenavir, aprepitant, atazanavir, ciprofloxacin, diltiazem, erythromycin, fluconazole, fosamprenavir, grapefruit juice, imatinib, verapamil). The dose can be increased to 10 mg in these patients if necessary for efficacy [see Clinical Pharmacology (12.3)].

CYP3A Inducers

Suvorexant exposure can be substantially decreased when co-administered with strong CYP3A inducers (e.g., rifampin, carbamazepine and phenytoin). The efficacy of BELSOMRA may be reduced [see Clinical Pharmacology (12.3)].

7.3 Effects of BELSOMRA on Other Drugs

Digoxin

Concomitant administration of BELSOMRA with digoxin slightly increased digoxin levels due to inhibition of intestinal P-gp. Digoxin concentrations should be monitored when co-administering BELSOMRA with digoxin [see Clinical Pharmacology (12.3)].

8.6 Patients with Compromised Respiratory Function

Effects of BELSOMRA on respiratory function should be considered if prescribed to patients with compromised respiratory function.

Obstructive Sleep Apnea

The respiratory depressant effect of BELSOMRA was evaluated after one night and after four consecutive nights of treatment in a randomized, placebo-controlled, 2-period crossover study in patients (n=26) with mild to moderate obstructive sleep apnea. Following once-daily doses of 40 mg, the mean 8 Apnea/Hypopnea Index treatment difference (suvorexant-placebo) on Day 4 was 2.7 (90% CI: 0.22 to 5.09), but there was wide inter- and intra-individual variability such that clinically meaningful respiratory effects of BELSOMRA in obstructive sleep apnea cannot be excluded. BELSOMRA has not been studied in patients with severe obstructive sleep apnea [see Warnings and Precautions (5.5)].

Chronic Obstructive Pulmonary Disease

The respiratory depressant effect of BELSOMRA was evaluated after one night and after four consecutive nights of treatment in a randomized, placebo-controlled, 2-period crossover study in patients (n=25) with mild to moderate chronic obstructive pulmonary disease (COPD). BELSOMRA (40 mg in non-elderly, 30 mg in elderly) had no respiratory depressant effects in patients with mild to moderate COPD, as measured by oxygen saturation. There was wide inter- and intra-individual variability such that clinically meaningful respiratory effects of BELSOMRA in COPD cannot be excluded. BELSOMRA has not been studied in patients with severe COPD [see Warnings and Precautions (5.5)].

8.7 Patients with Hepatic Impairment

No dose adjustment is required in patients with mild and moderate hepatic impairment. BELSOMRA has not been studied in patients with severe hepatic impairment and is not recommended for these patients [see Clinical Pharmacology (12.3)].

9 DRUG ABUSE AND DEPENDENCE

9.1 Controlled Substance

BELSOMRA contains suvorexant, a Schedule IV controlled substance.

9.2 Abuse

Abuse of BELSOMRA poses an increased risk of somnolence, daytime sleepiness, decreased reaction time and impaired driving skills [see Warnings and Precautions (5.1)]. Patients at risk for abuse may include those with prolonged use of BELSOMRA, those with a history of drug abuse, and those who use BELSOMRA in combination with alcohol or other abused drugs. Drug abuse is the intentional non-therapeutic use of an over-the-counter or prescription drug, even once, for its rewarding psychological or physiological effects. Drug addiction is a cluster of behavioral, cognitive, and physiological phenomena that may develop after repeated abuse of a prescription or over-the-counter drug, including: a strong desire to take the drug, difficulties in controlling drug use, persisting in drug use despite harmful consequences, a higher priority given to drug use than to other activities and obligations, as well as the possibility of the development of tolerance or development of physical dependence (as manifest by a withdrawal syndrome). Drug abuse and drug addiction are separate and distinct from physical dependence and tolerance (for example, abuse or addiction are not always accompanied by tolerance or physical dependence). In an abuse liability study conducted in recreational polydrug users (n=36), suvorexant (40, 80 and 150 mg) produced similar effects as zolpidem (15, 30 mg) on subjective ratings of "drug liking" and other measures of subjective drug effects. Because individuals with a history of abuse or addiction to alcohol or other drugs may be at increased risk for abuse and addiction to BELSOMRA, follow such patients carefully.

9.3 Dependence

Physical dependence is a stare that develops as a result of physiological adaptation in response to repeated drug use. Physical dependence manifests by drug class-specific withdrawal symptoms after abrupt discontinuation or a significant dose reduction of a drug. In completed clinical trials with BELSOMRA, there was no evidence for physical dependence with the prolonged use of BELSOMRA.

There were no reported withdrawal symptoms after discontinuation of BELSOMRA.

The following warnings are of particular concern: "Do not drive, operate heavy machinery, do other dangerous activities, or do other activities that require clear thinking after taking BELSOMRA," and "Do not take unless you are able to stay in bed a full night (at least 7 hours) before you must be active again."

In addition to the fact that all of the above medications (categories 1-10), whether indicated for sleep or a variety of other biological conditions, have their own significant list of side effects and risks, there is a lack of specificity attached to these medications. This means that all of these medications, whether indicated for sleep or for a variety of other biological conditions, only work on an unpredictable percentage or segment of the population. Alternative medication teaches us that there is a whole category of approaches that have less side effects. Holistic approaches to improve sleep include relaxation techniques, cognitive behavioral therapy for sleep, counting sheep, using the bedroom only for sleep, listening to music, watching television, exercise, hypnosis, and/or hard work before sleep, etc. While these approaches have very limited side effects, they also have very limited benefits and those benefits are only effective for a very limited percentage of the population as well. Although all of the medications and procedures noted above are known to benefit a certain percentage of the population, that percentage of the population is never well-defined by a biological procedure or technique and only discovered by trial and error.

Phosphodiesterase type 5 (PDE5) is an enzyme from the phosphodiesterase class found in various tissues such as the corpus cavernosum, the lung, and the retina, and which also play a role in the cardiovascular system. The 3',5'-cyclic nucleotide phosphodiesterases (PDEs) comprise a large class of enzymes divided into at least eleven different families which are structurally, biochemically and pharmacologically distinct from one another. The enzymes within each family are commonly referred to as isoenzymes, or isozymes. Further diversity among the isoenzymes results from differential splicing and post-translational processing of those gene products. PDE5 is characterized by selective, high affinity hydrolytic degradation of the second messenger cyclic nucleotide, guanosine 3'5'-cyclic monophosphate (cGMP).

The Latin term impotentia coeundi describes the simple inability to insert the penis into the vagina. The term is now mostly replaced by more precise terms, such as erectile dysfunction (ED). The study of erectile dysfunction within medicine is covered by andrology, a sub-field within urology. Research indicates that erectile dysfunction is common, and it is suggested that approximately 40% of males suffer from erectile dysfunction or impotence, at least occasionally (Schouten et al., 2010, J. Sex. Med. 7(7):2547-2553). Erectile dysfunction, defined as an inability to achieve an erection that is capable of helping a male engage in sexual intercourse, is a specific problem, primarily beginning in men 40 years of age or older, increasing in frequency with age, affecting a significant number of men as they age. Erectile dysfunction (ED), or impotence, is sexual dysfunction characterized by the inability to develop or maintain an erection of the penis during sexual activity. A penile erection is the hydraulic effect of blood entering and being retained in sponge-like bodies within the penis. The process is most often initiated as a result of sexual arousal, when signals are transmitted from the brain to nerves in the penis. The most important organic causes of ED are cardiovascular disease and diabetes, neurological problems (for example, trauma from prostatectomy surgery), hormonal insufficiencies (hypogonadism) and drug side effects. Psychological impotence is where erection or penetration fails due to thoughts or feelings (psychological reasons) rather than physical causes. Erectile dysfunction can have severe psychological consequences as it can be tied to relationship difficulties and masculine self-image. Besides treating the underlying causes such as potassium deficiency or arsenic contamination of drinking water, the first line treatment of erectile dysfunction most often consists of a trial of PDE5 inhibitors (Montague et al., 2005, J. Urol. 174(1):230-239).

PDE5 inhibitors were first targeted to treat pulmonary hypertension and then marketed to treat erectile dysfunction (ED). Phosphodiesterase 5 inhibitors, including, but not limited to, avanafil, lodenafil, mirodenafil, sildenafil, tadalafil, vardenafil, udenafil, zaprinast, icariin and benzamidenafil. Sildenafil (Viagra), tadalafil (Cialis), vardenafil (Levitra, Staxyn) and Stendra (avanafil) are specifically indicated for erectile dysfunction in males, only. A whole series of PDE5 inhibiting substances are known from the prior art and are described as potent and effective substances for the treatment of erectile dysfunction. By inducing relaxation of the vasculature within the corpus cavernosum of the penis, they increase the blood flow, thereby inducing tumescence of the penis. Relaxation of the vasculature is initiated by the release of NO from adrenergic neurons which subsequently activates the guanylyl cyclase of smooth muscle cells of the vessels of the corpus cavernosum. Once activated guanylyl cyclase synthesizes the second messenger cGMP which mediates the relaxation of the cell. PDE5 inhibitors prevent the degradation of cGMP by phosphodiesterase 5, thereby prolonging and enhancing the effects of cGMP. It has been demonstrated in several animal models and recently in several clinical trials that PDE5 inhibitors reduce the symptoms of pulmonary hypertension and commencing right-heart failure (Michelakis et al., 2003, Circulation 108: 2066; Ghofrani et al., 2003, J. Am. Coll. Cardiol. 42: 158; Ghofrani et al., 2002, Lancet 360: 895; Ghofrani et al., 2003, AJRCCM 167(8):1139). Furthermore, despite the fact that the mode of action is not clear, it has been shown that the PDE5 inhibitor sildenafil (Viagra,®) induces neurogenesis and promotes functional recovery after stroke in rats (Zhang et al., 2002, Stroke 33:2675-2680; Zhang et al., 2003, Circ. Res. 92(3):308). In a dog model of congestive heart failure it has been shown that chronic administration of a phosphodiesterase type 5 inhibitor suppresses renal production of endothelin-1 (Yamamoto et al., 2002, Olin. Sci. (Lund.) 103:258S). In addition sildenafil has been shown to relax epicardial coronary arteries of patients with coronary artery disease (Halcox et al., 2002, J. Am. Coll. Cardiol., 40:1232) and some animal studies suggest that sildenafil might work in diabetic gastropathy (Bianco et al., 2002, Diabetes Care, 25:1888) in which nNOS expression and activity seems to be reduced (Watkins et al., 2000, J. Olin. Invest., 106:373).

There is a need in the art for novel methods of treating insomnia, in particular methods which avoid manipulating the central nervous system, and with less chances of minor and major side effects, and less chance of abuse or addiction. This invention fulfills this need.

SUMMARY OF THE INVENTION

The invention provides a method of treating insomnia in a subject, the method comprises administering an effective amount of a phosphodiesterase 5 (PDE5) inhibitor to a subject in need thereof. In one embodiment, the PDE5 inhibitor is selected from the group consisting of avanafil, lodenafil, mirodenafil, sildenafil, tadalafil, vardenafil, udenafil, zaprinast, icariin and benzamidenafil. In one embodiment, the PDE5 inhibitor is sildenafil or a salt thereof. In another embodiment, the PDE5 inhibitor is sildenafil citrate. In another embodiment, the PDE5 inhibitor is avanafil or a salt thereof. In another embodiment, the PDE5 inhibitor is lodenafil or a salt thereof. In another embodiment, the PDE5 inhibitor is mirodenafil or a salt thereof. In another embodiment, the PDE5 inhibitor is tadalafil or a salt thereof. In another embodiment, the PDE5 inhibitor is vardenafil or a salt thereof. In another embodiment, the PDE5 inhibitor is udenafil or a salt thereof. In another embodiment, the PDE5 inhibitor is zaprinast or a salt thereof. In another embodiment, the PDE5 inhibitor is icariin or a salt thereof. In another embodiment, the PDE5 inhibitor is benzamidenafil or a salt thereof. In another embodiment, administration of an effective amount of a phosphodiesterase 5 (PDE5) inhibitor to a subject in need thereof further treats erectile dysfunction (ED).

In one embodiment of the method of the invention, insomnia is associated with sleep onset or difficulty falling asleep. In another embodiment, insomnia is associated with sleep maintenance or difficulty staying asleep. In another embodiment, insomnia is middle insomnia. In another embodiment, insomnia is associated with early morning awakening or waking up too early. In another embodiment, insomnia is associated with nonrestorative sleep or poor quality sleep. In another embodiment, insomnia is chronic insomnia. In another embodiment, insomnia is acute insomnia. In one embodiment, insomnia is primary insomnia co-morbid with another condition. In another embodiment, the other condition with which primary insomnia is co-morbid is erectile dysfunction (ED).

In one embodiment of the method of the invention, the administering step is selected from the group consisting of oral administration, sublingual administration, buccal administration, transdermal administration, nasal administration, subcutaneous administration and intramuscular administration. In one embodiment, the administering step comprises the use of a dosage form selected from the group consisting of a transmucosal tablet, a liquid, a capsule and a film.

In one embodiment of the method of the invention, the effective amount of a phosphodiesterase 5 (PDE5) inhibitor to be administered to a subject in need thereof is between less than 1 mg and 120 mg. In another embodiment, the effective amount is between 5 mg and 95 mg. In another embodiment, the effective amount is between 10 mg and 90 mg. In another embodiment, the effective amount is between 15 mg and 85 mg. In another embodiment, the effective amount is between 20 mg and 70 mg. In another embodiment, the effective amount is between 25 mg and 65 mg. In another embodiment, the effective amount is between 30 mg and 55 mg. In another embodiment, the effective amount is between 25 mg and 75 mg. In another embodiment, the effective amount is between 80 mg and 120 mg. In another embodiment, the effective amount is about 100 mg or 3 g.

In one embodiment, the subject is a male human.

DETAILED DESCRIPTION OF THE INVENTION

This invention is related to the unexpected discovery of a novel approach to treating insomnia by administration of a phosphodiesterase 5 (PDE5) inhibitor. Treating insomnia is therefore a new and unexpected major indication for PDE5 inhibitors. This invention aims to address all types of insomnia, e.g., insomnia associated with trouble falling asleep (sleep onset—difficulty falling asleep—DFA), trouble staying asleep (sleep maintenance—middle insomnia—MI), waking up too early (early morning awakening—EMA), and poor quality sleep (nonrestorative sleep).

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The articles "a" and "an" are used herein to refer to one or to more than one (i.e., to at least one) of the grammatical object of the article. By way of example, "a PDE5 inhibitor" means one PDE5 inhibitor or more than one PDE5 inhibitor.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A "disease" is a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. A disease or disorder is "alleviated" if the severity of a symptom of the disease or disorder, the frequency with which such a symptom is experienced by a patient, or both, is reduced.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "treatment" or "treating" encompasses prophylaxis and/or therapy. Accordingly the compositions and methods of the present invention are not limited to therapeutic applications and can be used in prophylaxis ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

Generally, an "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound. As used herein, the term "pharmaceutically effective amount" refers to a dose or quantity that causes improvement in at least one objective or subjective sleep parameter deficiency associated with insomnia including, but not limited to: difficulty falling asleep; difficulty maintaining sleep; waking up too early; decrease in total sleep time; persistent waking after sleep onset; and poor sleep quality. Although the present invention calls for methods of treating insomnia, some primary sleep disorders, such as circadian rhythm disorders, include insomnia as a component of the disorder. Thus, the term "insomnia" should be understood to also include the insomnia component of these disorders.

Insomnia can be described as primary, secondary, or co-morbid. Primary insomnia involves sleep parameter deficiencies not attributable to a medical, environmental, or psychiatric cause. Secondary insomnia includes sleep parameter deficiencies that are associated with another condition. Co-morbid insomnia includes primary insomnia concomitant with one or more other conditions. Insomnia can be further characterized as transient, acute or short-term, and chronic. Transient insomnia refers to sleep parameter deficiencies lasting a few nights. Acute or short-term insomnia refers to sleep parameter deficiencies lasting less than a month. Chronic insomnia refers to sleep parameter deficiencies lasting at least one month.

As used herein, the term "PDE5 inhibitor," unless stated otherwise or specifically designated, refers to avanafil, lodenafil, mirodenafil, sildenafil, tadalafil, vardenafil, udenafil, zaprinast, icariin, benzamidenafil, and other PDE5 inhibitors known or yet to be discovered, their pharmaceutically acceptable salts and their pharmaceutically acceptable derivatives. Unless stated otherwise or specifically designated, the term "PDE5 inhibitor" refers to isomers and prodrugs thereof.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, a "peptidomimetic" is a compound containing non-peptidic structural elements that is capable of mimicking the biological action of a parent peptide. A peptidomimetic may or may not comprise peptide bonds.

As used herein, the term "instructional material" refers to a publication, a recording, a diagram, or any other medium of expression which can be used to communicate the usefulness of the PDE5 inhibitor or composition thereof in a kit for identifying, diagnosing or alleviating or treating insomnia, or insomnia and ED. The instructional material of the kit may, for example, be affixed to a container that contains the PDE5 inhibitor or a composition thereof, or be shipped together with a container that contains the PDE5 inhibitor or a composition thereof. Alternatively, the instructional material may be shipped separately from the container with the intention that the recipient uses the instructional material and the PDE5 inhibitor or composition thereof compound cooperatively.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention relates to the unexpected discovery of effectively using a PDE5 inhibitor to treat insomnia. The invention relates to the promotion of male erection by means of a PDE5 inhibitor, followed by sexual intercourse, masturbation, ejaculation, or orgasm, which in turn will lead to post orgasmic sedation/somnolence/sleep (POS), also known as recovery phase sedation/somnolence/sleep (RPS).

In one aspect, the invention relates to a method for treating insomnia with a PDE5 inhibitor. The method involves administering a pharmaceutically effective amount of a PDE5 inhibitor to an individual suffering from insomnia. In one aspect, the individual is suffering from insomnia. In another aspect, the individual is suffering from chronic insomnia. In yet another aspect, the individual is suffering from acute insomnia. In one embodiment, the individual has insomnia associated with trouble falling asleep. In another embodiment, the individual suffers from insomnia associated with trouble staying asleep, or maintaining sleep. In another embodiment, the individual suffers from insomnia associated with waking up too early. In another embodiment, the individual suffers from insomnia as manifested through poor quality sleep, or nonrestorative sleep. In one aspect, the individual is suffering from primary insomnia co-morbid with another condition. In another aspect, the individual is suffering from primary insomnia co-morbid with ED.

In one aspect, the invention targets the use of phosphodiesterase 5 inhibitors in men for the treatment of insomnia. This approach to treating insomnia is through a well-defined biological mechanism and not a treatment for insomnia that is only discovered by trial and error, and it is an approach that is exclusive to males. In one aspect, the invention relates to a method for treating insomnia ill patients that also suffer from an erectile dysfunction (ED). The method involves administering a pharmaceutically effective amount of a PDE5 inhibitor to an individual suffering from primary insomnia and ED. In one embodiment, the targeted population is different from the population with ED. In another embodiment, the targeted population is the same as the population targeted for ED. In another embodiment, the population targeted only partially overlaps with the population targeted for ED. While perhaps insomnia is more common in women than in men, and more common in the elderly, this still leaves many men at risk for insomnia who will be able to benefit from this biological approach.

In one aspect, the invention is an improvement over the art because the underlying pharmacologic intervention avoids, as its primary focus, manipulating the central nervous system. As result there are less chances of minor and major side effects, less chances of abuse or addiction, and at the same time there is a greater likelihood to promote positive interaction between significant others. In one embodiment, the invention is better than the prior art because it is using compounds whose prior indication has resulted in so much usage that the side effects are known and overall display a much better side effect profile than the following known alternatives: 1) benzodiazepine, short acting medications; Ativan (lorazepam), Xanax (alprazolam), Librium (chlordiazepoxide), Halcion (triazolam), Restoril (temazepam), Serax (oxazepam), Prosom (estazolam); 2) benzodiazepine and sedative hypnotics, long acting medications: Valium (diazepam), Dalmane (flurazepam), Klonopin (clonazepam), chloral hydrate, Doral (quazepam); 3) non-benzodiazepine hypnotics: Sonata (zaleplon), Ambien (zolpidem), Rozerem (ramelteon), Lunesta (eszopiclone); 4) antihistamine: Atarax (hydroxyzine HCL), Vistaril (hydroxyzine pamoate, Benadryl (diphenhydramine), Unisom (doxylamine); 5) melatonin activating agents: Rozerem (Ramelteon); 6) barbiturates: Phenobarbital, Seconal, Tuinal; 7) natural substances and OTC preparations: Tryptophan; Melatonin; valerian root; kava; tryptophan and 5-L-5-hydroxytryptophan; chamomile tea; lip balm; 8) anti-depressants: Doxepin, trazodone, amitriptyline, mirtazapine; 9) antipsychotics: Seroquel, Zyprexa; and 10) Orexin Inhibitors: Belsomra (suvorexant).

In one aspect, the invention relates to a method of treating insomnia involving medication, wherein the medication can be taken in advance, so it has the quality of always being available to help to treat insomnia. In one embodiment, the medication is taken days in advance. In another embodiment, the medication is taken only when insomnia is an issue. Unlike the above medications and procedures in which everyone with insomnia is targeted but only a few respond, we are specifically interested in targeting a population already known to be able to benefit from a specific pharmacologic pathway to help with insomnia. While perhaps insomnia is more common in women than in men, and more common in the elderly, this still leaves many men at risk for insomnia that might benefit from this pathway. The invention targets that particular population by using a pharmacological agent previously indicated to work on a non-insomnia problem and will be using this non-insomnia mechanism for an entirely different indication. In one aspect, the invention relates to the fact that by hastening onset to sleep, sexual intercourse promotes better relationships. Therefore for many men, sedation after intercourse and/or after orgasm is a significant component of the orgasm. It is not specifically related to the ability to achieve an erection, it is related to the orgasm itself. In one embodiment, the targeted population for invention is men who are known to have or to have had recovery phase/post-coital sedation/somnolence/sleep, i.e., men who are known to have sedation and/or to fall asleep after orgasm.

Pharmaceutical Compositions and Formulations

The invention also encompasses the use of pharmaceutical compositions including PDE5 inhibitors or salts thereof to practice the methods of the invention. Such a pharmaceutical composition may consist of at least one compound or conjugate of the invention or a salt thereof in a form suitable for administration to a subject, or the pharmaceutical composition may comprise at least one compound or conjugate of the invention or a salt thereof, and one or more pharmaceutically acceptable carriers, one or more additional ingredients, or some combination of these. The compound or conjugate of the invention may be present in the pharmaceutical composition in the form of a physiologically acceptable salt, such as in combination with a physiologically acceptable cation or anion, as is well known in the art.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. In an embodiment, the pharmaceutical compositions useful for practicing the methods of the invention may be administered to deliver a dose of between 1 ng/kg/day and 120 mg/kg/day. In another embodiment, the pharmaceutical compositions useful for practicing the invention may be administered to deliver a dose of between 1 ng/kg/day and 500 mg/kg/day.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one aspect, the invention relates to a method for treating insomnia by administering a PDE5 inhibitor. In one embodiment, the PDE5 inhibitor is selected from the group consisting of avanafil, lodenafil, mirodenafil, sildenafil, tadalafil, vardenafil, udenafil, zaprinast, icariin and benzamidenafil. In one embodiment, the PDE5 inhibitor is avanafil. In another embodiment, the PDE5 inhibitor is lodenafil. In another embodiment, the PDE5 inhibitor is mirodenafil. In another embodiment, the PDE5 inhibitor is sildenafil. In another embodiment, the PDE5 inhibitor is tadalafil. In another embodiment, the PDE5 inhibitor is vardenafil. In another embodiment, the PDE5 inhibitor is udenafil. In another embodiment, the PDE5 inhibitor is zaprinast. In another embodiment, the PDE5 inhibitor is icariin. In another embodiment, the PDE5 inhibitor is benzamidenafil. In one embodiment, the PDE5 inhibitor is selected from the group consisting of a salt of avanafil, a salt of lodenafil, a salt of mirodenafil, a salt of sildenafil, a salt of tadalafil, a salt of vardenafil, a salt of udenafil, a salt of zaprinast, a salt of icariin and a salt of benzamidenafil. In one embodiment, the PDE5 inhibitor is sildenafil citrate. As one skilled in the art would readily recognize, the method of the invention may include other PDE inhibitors such as for example: roflumilast, cilomilast, pimobendan, GSK256066, PF-2545920, apremilast (CC-10004), cilostazol, milrinone, S-(+)-rolipram, aminophylline, fenspiride HCl, deltarasin, luteolin, rolipram, anagrelide HCl, irsogladine, doxofylline, dipyridamole, and dyphylline.

In one embodiment, the compositions of the invention are formulated using one or more pharmaceutically acceptable excipients or carriers. In one embodiment, the pharmaceutical compositions of the invention comprise a therapeutically effective amount of a PDE5 inhibitor or conjugate thereof and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, vaginal, parenteral, nasal, intravenous, subcutaneous, ophthalmic, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other PDE5 or PDE inhibitors, or other insomnia or ED drugs.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and combinations thereof.

Liquid suspensions may be prepared using conventional methods to achieve suspension of the PDE5 inhibitor in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropyl methylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethylene-oxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the PDE5 inhibitor in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil in water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

The invention provides for a method of treating insomnia wherein the PDE5 inhibitor or other medication is administered immediately before alleviation of insomnia is sought, or in advance, for example several days in advance. Accordingly, in one aspect the invention provides for controlled release, sustained, delayed or extended release formulations and delivery systems. The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer than the same amount of agent administered in bolus form. Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition over a shortened period of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects. Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

For sustained release, the PDE5 inhibitors may be formulated with a suitable polymer or hydrophobic material that provides sustained release properties. As such, the PDE5 inhibitors for use within the method of the invention may be administered in the form of microparticles, for example, by injection or in the form of wafers or discs by implantation. Controlled or sustained release formulations of a PDE5 inhibitor pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropyl methyl cellulose, other polymer matrices, gels, permeable membranes, osmotic systems, multilayer coatings, micro-particles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Dosage and Administration

In one aspect, the invention relates to a method for treating insomnia including administering a PDE5 inhibitor to an individual, wherein the administering step can be oral administration, sublingual administration or buccal administration. In one embodiment, oral administration comprises the use of a dosage form selected from the group consisting of a transmucosal tablet, a liquid, a capsule, and a film. In other embodiments, the PED5 inhibitor can be administered transdermally, nasally, subcutaneously, or intramuscularly.

Administration of the compositions of the present invention to a subject, preferably a mammal, more preferably a human, may be carried out using known procedures, at dosages and for periods of time effective to prevent or treat insomnia. An effective amount of a PDE5 inhibitor necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 mg/kg to about 5,000 mg/kg of body weight/per day. One of ordinary skill in the art would be able to study the relevant factors and make the determination regarding the effective amount of the therapeutic compound without undue experimentation.

Actual dosage levels of the PDE5 inhibitor in the pharmaceutical compositions of this invention may be varied so as to obtain an amount of the active ingredient that is effective to achieve the desired therapeutic response for a particular subject, composition, and mode of administration, without being toxic to the subject. A medical doctor, e.g., physician, having ordinary skill in the art may readily determine and prescribe the effective amount of the pharmaceutical composition required. For example, the physician could start doses of the PDE5 inhibitor employed in the pharmaceutical composition at levels lower than that required in order to achieve the desired therapeutic effect and gradually increase the dosage until the desired effect is achieved. In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the PDE5 inhibitor employed and the particular therapeutic effect to be achieved, and (b) the limitations inherent in the art of compounding/formulating such a PDE5 inhibitor for the treatment of insomnia in a subject.

In one aspect of the invention, the PDE5 inhibitor employed can be administered in the range of less than about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, less than about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between. In some embodiments, the dose of PDE5 inhibitor is from less than about 1 mg and about 2,500 mg. In some embodiments, a dose of PDE5 inhibitor used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. In another embodiment, the dose of PDE5 inhibitor is from about 80 mg to about 120 mg. In some embodiments, the effective amount is about 100 mg e.g., when administered orally or about 3 g e.g., when administered via an injection.

In another aspect of the invention, a second therapeutic agent (i.e., a drug used for treating insomnia or another disease or disorder) as described herein can be employed in the pharmaceutical composition. The second therapeutic agent is a drug or compound for enhancing sleep quantity and treating insomnia, including e.g., at least one therapeutic agent selected from anxiolytics, antidepressants, hypnotics (benzodiazepines as well as non-benzodiazepines), sedatives, antihypertensives, analgesics, dopaminergic agonists, antipsychotics, minor tranquilizers, anorectics and anti-inflammatory drugs. Examples of such additional therapeutic agents are adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, valproate, venlafaxine, zaleplon, zolazepam, zolpidem, zopiclone and salts thereof, and combinations thereof.

In one aspect of the invention, the second therapeutic agent employed can be administered in the range of less than about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, less than about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between. In some embodiments, the dose of the second therapeutic agent is from less than about 1 mg and about 2,500 mg. In some embodiments, a dose of the second therapeutic agent used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The composition of a therapeutically effective amount of the PDE5 inhibitor and the second therapeutic agent can be configured as a sleeping pill composition having a delayed release formulation. The delayed release formulation can be used to achieve a desired therapeutic response after a particular period of time. For example, at the time of administration, the PDE5 inhibitor is initially released to produce a desired therapeutic effect. The second therapeutic agent, for example, a therapeutic sleeping agent, can be subsequently released after a period of time to reduce the symptoms of insomnia. The delayed release serves to produce the desired therapeutic effect of reducing the symptoms of insomnia at a desired period of time such as in the middle of the night, when insomnia symptoms may arise. Such a delayed release formulation can reduce undesirable side effects and facilitate optimal delivery of a drug composition. In one embodiment, the method of the present invention further comprises administering an effective amount of a therapeutic sleeping agent in a delayed release formulation.

In one embodiment, the pharmaceutically effective amount of PDE5 inhibitor can be from less than about 1 mg to 120 mg. In other embodiments, the pharmaceutically effective amount of PDE5 inhibitor is from 5 mg to 95 mg, from 10 mg to 90 mg, from 15 mg to 85 mg, from 20 mg to 70 mg, from 25 mg to 65 mg, from 30 mg to 55 mg, and all doses between the above listed ranges. In another embodiment, the pharmaceutically effective amount of PDE5 inhibitor is from 25 mg to 75 mg. In another embodiment, the pharmaceutically effective amount of PDE5 inhibitor is from 80 mg to 120 mg. In one embodiment, the PDE5 inhibitor is administered in a pharmaceutically effective amount to treat insomnia wherein the pharmaceutically effective amount does not cause undesirable side effects.

In another embodiment, the PDE5 inhibitor is administered in a pharmaceutically effective amount to treat insomnia wherein the pharmaceutically effective amount is incrementally released over an extended period of time. For example, the PDE5 inhibitor can be administered by injection once a month wherein the pharmaceutically effective amount is a high dose incrementally released daily for a month. In one embodiment, the high dose of PDE5 inhibitor can be from less than about 1 g to 10 g. In other embodiments, the high dose of PDE5 inhibitor is from 2 g to 9 g, from 3 g to 8 g, from 4 g to 7 g, from 5 g to 6 g, and all doses between the above listed ranges. In another embodiment, the high dose of PDE5 inhibitor is from 1 g to 5 g. In another embodiment, the high dose of PDE5 inhibitor is from 2 g to 4 g.

As one skilled in the art would understand, a pharmaceutically effective amount of a PDE5 inhibitor that does or does not cause undesirable side effects may comprise different doses based on an individual's characteristics including age, weight, drug tolerance, sex, ethnicity, and various genetic factors involved in the metabolism of PDE5 inhibitors. Accordingly, embodiments of the present method further comprise adjusting the dose of PDE5 inhibitor based on one or more factors of the group consisting of PDE5 inhibitor metabolite(s) levels, age, weight, drug tolerance, sex, and presence of side effects upon waking.

Kits

In one embodiment, the present invention is directed to a packaged pharmaceutical composition comprising a container holding a therapeutically effective amount of a PDE5 inhibitor or conjugate thereof, alone or in combination with a second pharmaceutical agent; and instructions for using the compound or conjugate to treat, prevent, or reduce one or more symptoms of insomnia in a subject. In another embodiment, the pharmaceutical composition treats, prevents, or reduces one or ore symptoms of insomnia and ED in a subject.

In another embodiment, the instructions, e.g., instruction material, provide directions to a user for practicing the method described herein for treating insomnia in a subject. For example, the instructions communicate to a user the method of treating insomnia including administering an effective amount of a PDE5 inhibitor and engaging in sexual intercourse or masturbation, and achieving orgasm.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product, or be a separate instructional material. However, it should be understood that the instructions may contain information pertaining to the compound's ability to perform its intended function, e.g., treating or preventing a disease in a subject, or delivering an imaging or diagnostic agent to a subject.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein. Without further description, it is believed that one of ordinary skill in the art can, using the preceding description and the following illustrative examples, practice the claimed methods. The following working examples therefore, specifically point out the preferred embodiments of the present invention, and are not to be construed as limiting in any way the remainder of the disclosure.

Example 1: Administration of PDE5 Inhibitors as a Method of Treating Middle Insomnia in a 40-Year-Old Male Patient A 40-year-old male who chronically suffers from middle insomnia—trouble staying asleep (sleep maintenance). He has no erectile dysfunction, but he uses PDE5 inhibitors (phosphodiesterase 5 inhibitors) because of their ability to promote post orgasmic somnolence (POS). The differential diagnosis of his insomnia is unclear. His middle insomnia is either related to his Major Depressive Episode, Generalized Anxiety Disorder, diabetic neuropathy, arthritic condition or to his spouse's sleep apnea-related snoring. Once awake, however, it has been very difficult for him to fall back to sleep. Numerous pharmacologic agents including all of the following categories with their comprehensive warnings have frightened him or have significant side effects: 1) Benzodiazepine (short acting medications): Ativan (lorazepam), Xanax (alprazolam), Librium (chlordiazepoxide), Halcion (triazolam), Restoril (temazepam), Serax (oxazepam), Prosom (estazolam); 2) Benzodiazepine and Sedative hypnotics (long acting medications): Valium (diazepam), Dalmane (flurazepam), Klonopin (clonazepam), chloral hydrate, Doral (quazepam); 3) Non-benzodiazepine hypnotics: Sonata (zaleplon), Ambien (zolpidem), Rozerem (ramelteon), Lunesta (eszopiclone); 4) Antihistamine: Atarax (hydroxyzine HCL), Vistaril (hydroxyzine pamoate, Benadryl (diphenhydramine), Unisom (doxylamine); 5) Melatonin activating agents: Rozerem (Ramelteon); 6) Barbiturates: Phenobarbital, Seconal, Tuinal; 7) Natural substances and OTC preparations: Tryptophan; Melatonin; valerian root; kava; tryptophan and 5-L-5-hydroxytryptophan; chamomile tea; lip balm; 8) Anti-depressants: Doxepin, trazodone, amitriptyline, mirtazapine; 9) Antipsychotics: Seroquel, Zyprexa; 10) Orexin Inhibitors: Belsomra (suvorexant).

Having originally fallen asleep 4 hours ago, shortly after he had sexual intercourse with his now sleeping significant other, he awakens and cannot fall back to sleep. He knows that having sexual intercourse with his significant other would help promote sleep. He does not have time for lengthy foreplay, as he needs to get back to sleep quickly, and his significant other remains asleep. He is desirous of a rapidly achieved erection, either with intercourse or masturbation. He knows that an orgasm will bring help him to be able to rapidly achieve post orgasmic sedation/somnolence/sleep (POS), also [potentially] known as recovery phase sedation/somnolence/sleep (RPS).

Example 2: Method of Treating Major Aspects of Insomnia by Administration of a Phosphodiesterase Inhibitor Men could take this for all aspects of insomnia as follows: 1) Trouble falling asleep (sleep onset—difficulty falling asleep—DFA); 2) Trouble staying asleep (sleep maintenance—middle insomnia—MI); 3) Waking up too early (early morning awakening—EMA); 4) Poor quality sleep (nonrestorative sleep). In accordance with a preferred embodiment, the present invention provides a method for the treatment of male insomnia which comprises administering a pharmacologically effective amount of a composition comprising a phosphodiesterase inhibitor. The method further includes stimulating the penis to achieve orgasm.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A kit for practicing a method of treating insomnia in a subject, the kit comprising (1) at least an effective amount of a PDE5 inhibitor and (2) an instructional material instructing:
   (a) administration of an effective amount of the PDE5 inhibitor to a subject in need thereof; and
   (b) the subject to engage in sexual intercourse or masturbation until the subject achieves orgasm.

2. The kit of claim 1, wherein the PDE5 inhibitor is selected from the group consisting of sildenafil, avanafil, lodenafil, mirodenafil, tadalafil, vardenafil, udenafil, zaprinast, icariin, benzamidenafil, and any salt thereof.

3. The kit of claim 1, wherein the PDE5 inhibitor is sildenafil citrate.

4. The kit of claim 1, wherein the insomnia is associated with sleep onset, difficulty falling asleep, sleep maintenance, difficulty staying asleep, early morning awakening, waking up too early, nonrestorative sleep, or poor quality sleep.

5. The kit of claim 1, wherein the insomnia is middle insomnia, chronic insomnia, acute insomnia, or primary insomnia co-morbid with another condition.

6. The kit of claim 1, wherein the insomnia is primary insomnia co-morbid with erectile dysfunction.

7. The kit of claim 1, wherein the administration is selected from the group consisting of oral administration, sublingual administration, buccal administration, transdermal administration, nasal administration, subcutaneous administration, and intramuscular administration.

8. The kit of claim 7, wherein the the PDE5 inhibitor is present in the kit as a dosage form selected from the group consisting of transmucosal tablets, liquids, capsules, and films.

9. The kit of claim 1, wherein the effective amount is in the range of from 1 mg to 120 mg.

10. The kit of claim 1, wherein the effective amount is in the range of from 80 mg to 110 mg.

11. The kit of claim 1, wherein the effective amount is in the range of from 95 mg to 105 mg.

12. The kit of claim 1, wherein the effective amount is in the range of from 5 mg to 30 mg.

13. The kit of claim 1, wherein the effective amount is in the range of from 10 mg to 20 mg.

14. The kit of claim 1, wherein the effective amount is in the range of from 25 mg to 65 mg.

15. The kit of claim 1, wherein the effective amount is in the range of from 1 g to 10 g.

16. The kit of claim 1, wherein the effective amount is in the range of from 1 g to 5 g.

17. The kit of claim 1, wherein the effective amount is in the range of from 2 g to 4 g.

18. The kit of claim 1, further comprising at least an effective amount of a delayed release formulation of a therapeutic sleeping agent and the instructional material instructs administration of an effective amount of the delayed release formulation of a therapeutic sleeping agent to a subject in need thereof.

* * * * *